US009629616B2

(12) United States Patent
Guggenheim et al.

(10) Patent No.: US 9,629,616 B2
(45) Date of Patent: Apr. 25, 2017

(54) METHOD FOR DETECTION OF HEPATOCELLULAR CARCINOMA (HCC) USING AN OCTANOATE BREATH TEST

(71) Applicant: EXALENZ BIOSCIENCE LTD., Modi'in (IL)

(72) Inventors: Gil Guggenheim, Jerusalem (IL); Ilan Ben-Oren, Modi'in (IL); Avraham Hershkowitz, Nof Ayalon (IL); Yaron Ilan, Jerusalem (IL)

(73) Assignee: EXALENZ BIOSCIENCE LTD., Modi'in (IL)

( * ) Notice: Subject to any disclaimer, the term of this patent is extended or adjusted under 35 U.S.C. 154(b) by 598 days.

(21) Appl. No.: 14/054,421

(22) Filed: Oct. 15, 2013

(65) Prior Publication Data

US 2014/0033795 A1 Feb. 6, 2014

Related U.S. Application Data

(63) Continuation of application No. PCT/IL2012/050136, filed on Apr. 5, 2012.

(60) Provisional application No. 61/475,264, filed on Apr. 14, 2011.

(51) Int. Cl.
| | | |
|---|---|---|
| A61B 5/08 | (2006.01) | |
| A61B 10/00 | (2006.01) | |
| A61B 5/00 | (2006.01) | |
| G01N 33/497 | (2006.01) | |

(52) U.S. Cl.
CPC .............. *A61B 10/00* (2013.01); *A61B 5/082* (2013.01); *A61B 5/4244* (2013.01); *A61B 5/4842* (2013.01); *G01N 33/497* (2013.01)

(58) Field of Classification Search
None
See application file for complete search history.

(56) References Cited

U.S. PATENT DOCUMENTS

| | | | |
|---|---|---|---|
| 6,071,245 A | 6/2000 | Kohno et al. | |
| 6,186,958 B1 | 2/2001 | Katzman et al. | |
| 6,491,643 B2 | 12/2002 | Katzman et al. | |
| 6,656,127 B1 | 12/2003 | Ben-Oren et al. | |
| 6,778,269 B2 | 8/2004 | Fink et al. | |
| 8,512,258 B2* | 8/2013 | Ben Oren | A61K 49/00 600/531 |
| 8,622,920 B2* | 1/2014 | Ben-Oren | A61K 51/04 600/529 |
| 2001/0021815 A1 | 9/2001 | Katzman et al. | |
| 2003/0216660 A1 | 11/2003 | Ben-Oren et al. | |
| 2004/0152994 A1 | 8/2004 | Meier-Augenstein | |
| 2009/0131810 A1* | 5/2009 | Oren | A61K 49/00 600/532 |
| 2009/0215835 A1* | 8/2009 | Wilhelm | A61K 31/44 514/350 |

FOREIGN PATENT DOCUMENTS

| | | |
|---|---|---|
| JP | 61-017550 | 1/1986 |
| JP | 11-116503 | 4/1999 |
| WO | 99/12471 | 3/1999 |
| WO | 2007054940 A2 | 5/2007 |
| WO | 2009/111846 | 9/2009 |
| WO | 2009/117096 | 9/2009 |
| WO | 2009/152222 | 12/2009 |
| WO | 2010013235 A2 | 2/2010 |
| WO | 2010/062706 | 6/2010 |

OTHER PUBLICATIONS

Mizrahi M. et al. C-13 Breath Test Identifies Decreased Beta Oxidation . . . J of Hepatology 52(Suppl 1)S150, 2010.*
Chapman D. et al. A Comparison of the Oxidation of Octanoate-1-C14, -7-C14, and Butyrate-1-C14 by Neoplastic and Normal Mouse Tissues. Cancer Research vol. 14:372-6, 1954.*
Grattagliano I. et al. 13C Breath Tests for Clinical Investigation of Liver Mitochondrial Function. European J of Clinical Investigation 40:843-850.*
Shalev T. et al. Evaluation of the 13C Octanoate Breath Test as a Surrogate Marker of Liver Damage in Animal Models Digestive Disease Sciences 55(6)1589-1598 Jun. 2010.*
Braun et al., (2005) The unique breath ID test system diagnoses and predicts the extent of hepatic injury in patients with nonalcoholic fatty liver disease. Hepatology 42: 752A.
Grattagliano et al., (2010) 13C-breath tests for clinical investigation of liver mitochondrial function. Eur J Clin Invest 40(9): 843-850.
Kurosu et al., (2009) Sorafenib induces apoptosis specifically in cells expressing BCR/ABL by inhibiting its kinase activity to activate the intrinsic mitochondrial pathway. Cancer Res 69(9): 3927-3936.
Palmieri et al., (2009) Liver function as assessed by breath tests in patients with hepatocellular carcinoma. J Surg Res 157(2): 199-207.
Portincasa et al. (2010) Clinical Investigation of Liver Mitochondrial Function: A Role for 13C-Stable Isotope Breath Tests? Clujul Medical 83(Suppl 2): 23-26.
Schommartz et al., (1998) Significance of diagnostic parameters in [13C]octanoic acid gastric emptying breath tests. Isotopes Environ Health Stud 34(1-2): 135-143.
Van de Casteele et al., (2003) Oxidative breakdown of octanoic acid is maintained in patients with cirrhosis despite advanced disease. Neurogastroenterol Motil 15(2): 113-120.
Warburg (1956) On the origin of cancer cells. Science 123(3191): 309-314.
International Search Report and Written Opinion of the International Searching Authority Application No. PCT/IL2012/050136 Completed: Jul. 23, 2012; Mailing Date: Aug. 16, 2012 8 pages.

* cited by examiner

*Primary Examiner* — Ralph Gitomer
(74) *Attorney, Agent, or Firm* — The Roy Gross Law Firm, LLC; Roy Gross

(57) ABSTRACT

The present invention relates to methods and systems for diagnosis, prognosis and monitoring of hepatocellular carcinoma (HCC). Specifically, the present invention relates to the use of breath tests based on isotope-labeled octanoate in the detection and monitoring of HCC.

26 Claims, 9 Drawing Sheets

METHOD FOR DETECTION OF HEPATOCELLULAR CARCINOMA (HCC) USING AN OCTANOATE BREATH TEST

This application is a Continuation of PCT/IL2012/050136 filed on Apr. 5, 2012, which claims priority to U.S. Ser. No. 61/475,264 filed Apr. 14, 2011. Both applications are incorporated by reference into this application in their entirety.

FIELD OF THE INVENTION

The present invention relates to diagnosis, prognosis, monitoring and treatment of hepatocellular carcinoma (HCC). Specifically, the present invention relates to the use of breath tests based on isotope-labeled octanoate in the detection and monitoring of HCC.

BACKGROUND OF THE INVENTION

Hepatocellular carcinoma (HCC, also referred to as malignant hepatoma) is a primary malignancy of the liver. HCC most commonly appears in patients with chronic viral hepatitis (e.g. hepatitis B) and/or cirrhosis with any etiology. Non-alcoholic steatohepatitis (NASH) has also been found to be a risk factor for the development of HCC. Examples of other risk factors include high aflatoxins exposure and iron overload conditions such as hemochromatosis. In some cases, cryptogenic HCC is developed in patients with no history of liver disease or known risk factors.

HCC incidence worldwide is constantly increasing. In some parts of the world, such as in sub-Saharan Africa, China, Hong-Kong and Taiwan, HCC is a major health problem, probably due to high exposure to hepatitis viruses like B and C and to regional exposure to environmental pathogens.

The pathogenesis of HCC is not completely known, however mitochondrial dysfunction is suggested to be involved. HCC cells show genetic and metabolic alterations with a decreased mitochondrial function (Warburg O (1956). "On the origin of cancer cells". Science 123 (3191): 309-14).

Treatment of HCC may be directed towards a cure, or focused on relief of symptoms and prolongation of life. The type of treatment is typically selected according to the tumor size and stage. When the tumor is small (less than 2-3 cm), limited to one lobe of the liver, without evidence of invasion of the liver vasculature and in a well preserved liver function, surgical resection may be performed. Other treatment options include liver transplantation, radiofrequency ablation (RFA) and transarterial chemoembolization (TACE) (for treatment algorithms, see, for example, the Barcelona Clinic Liver Cancer (BCLC) Staging System). In RFA, radiofrequency energy is transmitted to the tumor via a needle electrode which is advanced into the tumor under image guidance (such as X-ray screening, CT scan or ultrasound). The radiofrequency waves passing through the needle lead to tumor destruction by thermal coagulation and protein denaturation. In TACE, chemotherapy is administered directly to the tumor via a catheter, and blood supply to the tumor is cut-off. In addition to the procedures described above, oral medicines may also be administered. For example, sorafenib tosylate (Nexavar™), an oral medicine that blocks tumor growth by activating the intrinsic mitochondrial pathway (Kurosu, "Sorafenib induces apoptosis specifically in cells expressing BCR/ABL by inhibiting its kinase activity to activate the intrinsic mitochondrial pathway", Cancer Research 2009 May 1; 69(9):3927-36.), is approved for patients with advanced HCC.

In general, small or slow growing tumors may be successfully treated if diagnosed early. However, early diagnosis is difficult, partially because most of the patients who develop HCC have no symptoms other than those related to their longstanding liver disease. Surveillance of high-risk groups, such as cirrhotic patients, is usually performed to facilitate early detection of HCC (see, for example, AASLD Guidelines).

The detection and diagnosis of HCC is typically based on imaging tests, serology tests and sometimes biopsy. Imaging tests include, for example, abdominal ultrasound, helical computed tomography (CT) scan, triple phase CT scan and magnetic resonance imaging (MRI). Serology tests include measurement of blood levels of alpha-fetoprotein (AFP), where high levels of AFP are associated with HCC. The typical strategy is 6-monthly surveillance with AFP and ultrasound.

Assessment of HCC is also performed as part of post-treatment monitoring. Evaluation of treatment efficacy and determination of active vs. inactive HCC are usually performed radiologically using contrast-enhanced CT or MRI. Exemplary contrast media is Lipiodol®, an iodized oily agent that is selectively retained within the tumor microvessels. Lack of vascular enhancement in the treated lesion is typically indicative of positive response to the treatment. AFP is not accurate enough as a follow-up tool, and the monitoring of AFP levels after therapy does not replace imaging. The ideal imaging interval is unknown, but initially a 3-4 month interval is commonly used to monitor HCC lesions after initial treatment.

The standard techniques for HCC diagnosis and follow-up have several drawbacks. For example, imaging methods based on CT or MRI, are considered expensive, must be performed in a hospital by a skilled practitioner, and associated with high radiation and side effects such as contrast-media-induced nephropathy in the case of CT/MRI. In addition, methods such as AFP measurements are insufficiently sensitive or specific.

Breath tests based on monitoring $^{13}CO_2$ levels, which is a by-product of metabolism of $^{13}C$-labeled substrates by the liver, have been proposed as a tool for evaluation of liver function. If the hepatic metabolism of a test compound results in the formation of carbon dioxide, and the appropriate carbon is labeled, the exhalation of labeled $CO_2$ (which is measurable, for example, in mass spectrometry or non-dispersive infrared analyzer), reflects the hepatic clearance of the original labeled compound and may be used to asses specific liver functions. For example, compounds metabolized by hepatocytes cytochrome P450 enzymes may be used in the assessment of liver microsomal function. Exemplary compound is methacetin. As another example, compounds that undergo metabolism in liver mitochondria may be used in the assessment of liver mitochondria function and may be used to detect certain liver conditions (see for example, Grattagliano et al. (2010) Eur J Clin Invest, 40 (9): 843-850 and Portincasa et al. (2010) Clujul Medical, 83: 23-26).

One exemplary molecule is ketoisocaproate (KICA), a compound that undergoes decarboxylation in liver mitochondria. Use of KICA breath tests in evaluation of liver function in HCC patients has been reported (Palmieri et al. (2009) Journal of Surgical Research 157, 199-207). In this study, the effect of two different HCC treatments on liver function was evaluated. Cirrhotic patients with and without HCC were tested using, inter alia, KICA decarboxylation. At baseline, patients with HCC had significantly lower $^{13}$C-KICA breath test values compared with healthy controls and cirrhotic patients without HCC. Minor but significant changes in $^{13}$C-KICA breath test values emerged between cirrhotic patients without HCC and healthy controls (lower values were observed for the cirrhotic patients without HCC compared to healthy control). The patients were treated by either TACE or RFA, after which $^{13}$C-KICA levels were again tested at day 1, day 30 and day 180. The authors summarized: "ketoisocaproate decarboxylation was unaffected by TACE but decreased after RFA (−27%, P<0.05)", and concluded: "RFA not TACE appears to spare residual (microsomal) liver mass, but induces such a transient stunning effect on mitochondrial function".

Another exemplary molecule that is metabolized by liver mitochondria is Octanoate. Octanoate is a medium chain fatty acid that enters mitochondria and undergoes β-oxidation generating acetyl coenzyme A (acetyl-CoA). Acetyl-CoA enters the Krebs cycle and is oxidized to $CO_2$ unless it is utilized for the synthesis of other energy-rich compounds.

WO 2007/054940, to the Applicant of the present invention, discloses breath test devices and methods for the evaluation of liver functional and metabolic capacity or to assess liver health and/or degree of liver injury. For example, a method of evaluating a liver condition is disclosed, the method includes on-line monitoring a metabolic product of octanoic acid, a salt or a derivative of octanoic acid, in a subject's breath after administering to the subject isotope labeled octanoic acid, a salt or a derivative thereof. As another example, a device for evaluating a liver condition is disclosed, the device includes one or more sensors adapted to monitor on-line an isotope level of a metabolic product of labeled octanoic acid, or a salt or a derivative thereof in a subject's breath and a controller adapted to sample measurements of the one or more sensors at a continuous mode. The method and device may be used in distinguishing between a non-alcoholic fatty liver and non-alcoholic steatohepatitis conditions in a subject.

WO 2010/013235, to the Applicant of the present invention, discloses breath test devices and methods that may be used for the evaluation of liver functional and metabolic capacity or to assess liver health and/or degree of liver injury. For example, a method of detecting abnormal beta-oxidation associated with insulin resistance or alcoholic liver disease or non-alcoholic fatty liver disease or metabolic syndrome is disclosed, the method includes monitoring a metabolic product of octanoic acid, a salt or a derivative of octanoic acid, in a subject's breath after administering to the subject isotope labeled octanoic acid, a salt or a derivative thereof.

The complexity of liver metabolism imposes challenges on assessing its function, and therefore interpretation of breath test results is not always straightforward. Examples of potential limitations for the interpretation of breath test results include the presence of confounding variables (e.g. exercise), the typology of gastric emptying kinetics, the hepatic first pass metabolism of the administered substrates, and the presence of competing pathways of elimination and metabolism of compounds. Additional factors that should be taken into account include, for example, the presence of mitochondrial metabolism occurring in organs other than the liver (extra hepatic metabolism, when hepatic metabolism is of interest, would negatively impact test relevance), possible dilution of exogenous labeled compound in a larger pool of unlabelled compound, and endogenous production of unlabelled $CO_2$ which can vary substantially from subject to subject. Furthermore, there are many factors that result in high intra- and inter-patient variability, and different disease etiologies may impact different functions of the liver and may result in a different breath test outcomes.

There still remains a need for cost effective, accurate and simple methods and systems for surveillance, detection, prognosis and monitoring response to treatment of hepatocellular carcinoma.

SUMMARY OF THE INVENTION

The present invention provides methods and systems for improved HCC detection, evaluation, and monitoring response to treatment, which utilize octanoate or salts or derivatives thereof.

The present invention discloses for the first time that the level of octanoate metabolism by liver mitochondria, as reflected in breath tests using isotope-labeled octanoate, correlates with the presence of active HCC, and can be used to detect and monitor HCC. In particular, it is now disclosed that lower values of isotope-labeled octanoate breath test (OBT), for example $^{13}$C-octanoate breath test, are indicative of active HCC. It was surprisingly found that significantly lower $^{13}$C-octanoate breath test values are observed for subjects having active HCC in comparison to subjects having inactive HCC and control subjects with no HCC. Subjects having inactive HCC exemplified herein below have undergone TACE treatment and were evaluated close after and up to 3 months after the procedure. The observed results are surprising, inter alia, in light of earlier publications stating that: "TACE did not induce an early fall of mitochondrial function, as observed for RFA, suggesting no specific interference of this procedure with mitochondrial function." (Palmieri et al. (2009) Journal of Surgical Research 157, 199-207).

The present invention further discloses that OBT values may be used for detection of HCC even in early stages. Remarkably, it was found that even in a patient with HCC<2 cm, which represents a very small part of the liver mass, OBT measurements are significantly reduced. The present invention further discloses that OBT values may be used in post-treatment follow-up of patients with HCC, for the assessment of response to treatment and/or recurrence of the disease.

The methods and systems of the present invention may be applicable for screening/surveillance and early detection of small and larger tumors. The methods and systems of the present invention may also be applicable for monitoring the response to several types of HCC treatments, for example, TACE and RFA treatments. OBT may also enable early detection of recurrence following resection of the tumor, or following liver transplantation.

According to one aspect, the present invention provides a method for HCC detection, determining a prognosis and/or follow-up in a subject, the method comprising:

(i) monitoring an isotope-labeled metabolic product of octanoate in exhaled breath of the subject following administration of an isotope-labeled octanoate;

(ii) comparing octanoate metabolism in the subject to a reference octanoate metabolism, wherein a significantly decreased octanoate metabolism is indicative of active HCC.

In some embodiments, the method further comprises normalization of the breath test values according to disease etiology, as detailed below. In additional or alternative embodiments, the method further comprises normalization of the breath test values according to a treatment, as detailed below. In some embodiments, the method further comprises distinguishing between active and inactive HCC based on the comparison.

The method according to embodiments of the present invention is useful for early detection of active HCC, for example, HCC smaller than 2 cm. The decrease in OBT in patients with small active HCC (e.g. <2 cm), which could be masked by inter and intra variability of the metabolism by the great majority of the liver mass, cannot be profoundly explained based on the prior art. Without wishing to be bound by any particular theory or mechanism of action, it may reflect a factor or factors secreted by the tumor cells that is/are affecting the overall mitochondrial function in the liver of these patients. Any type of therapy that counteracts this factor or these factors may have an effect on alleviation of the malignant process. Alternatively or additionally, it may be due to trapping of the octanoate in the tumor, for example into its hypervascularity regions or in the tumor cells or in between the cells and in vessels. The changes in vessels associated with the tumor might attribute to the enhancement of the effect beyond the direct mass of the tumor. The potential trapping effect may serve as a mean for delivering contrast agents or therapeutic agents to the tumor. A delivery mechanism to HCC may enable to achieve high concentration of a therapeutic agent in the tumor without systemic side effects.

The present invention addresses some of the limitations of prior art tests, for example, $^{13}$C-KICA breath tests. As opposed to KICA used in prior art, octanoate metabolism is not affected by the overall liver function and remains normal in cirrhotic patients. Advantageously, octanoate breath tests allow a greater differentiation between patients with impaired liver (due to fibrosis stage or cirrhosis) without HCC, that will have an octanoate metabolism similar to normal subjects and not already decreased due to reduced liver reserve like in KICA, and those with HCC.

As used herein, the term "octanoate" encompasses octanoate and salts or derivatives thereof, such as octanoic acid. The $^{13}$C-labeled "octanoate" is known by the generic name of sodium caprylate, sodium salt of caprylic acid. The IUPAC name for the sodium caprylate is 1-$^{13}$C-Octanoate Sodium. Additional synonyms include: 1-$^{13}$C-Octanoate Sodium; Sodium Octanoate, Octanoic Acid Sodium Salt, Sodium n-Octanoate, Sodium Octoate.

As used herein, "monitoring an isotope-labeled metabolic product of octanoate" refers to detecting and measuring a change in isotope ratio in exhaled breath of a subject over a predetermined period of time. The term "isotope ratio" refers to the ratio between the isotope selected for octanoate labeling and the naturally-abundant isotope. In some embodiments, monitoring is performed by continuous measurement over a predetermined period of time following a single administration of labeled octanoate. In other embodiments, the isotope ratio is measured in breath samples collected from the subject at periodic intervals following a single administration of labeled octanoate. According to these embodiments, a plurality of samples is collected over a predetermined period of time.

In some typical embodiments, the metabolic product is $CO_2$. In some embodiments, the isotope is selected from the group consisting of carbon-13, carbon-14 and oxygen-18. In some typical embodiments, the isotope is $^{13}$C.

In some embodiments, comparing octanoate metabolism in the subject to a reference octanoate metabolism comprises generating at least on of delta over baseline (DOB) curve, percentage dose recovery (PDR) curve and cumulative PDR (CPDR) curve for the subject, and comparing at least one parameter of said DOB, PDR or CPDR to at least one parameter of reference DOB, PDR, CPDR or a combination thereof.

In some embodiments, comparing octanoate metabolism in the subject to a reference octanoate metabolism comprises generating PDR curve and comparing at least one parameter of said PDR curve to at least one parameter of a reference PDR.

In some embodiments, the at least one parameter is selected from the group consisting of PDR maximum level (peak height), time of appearance of the peak (time to peak) and the slope of rate of metabolism. Each possibility represents a separate embodiment of the invention.

In some specific embodiments, the parameter is peak height. According to these embodiments, a decreased peak height is indicative of HCC.

In additional specific embodiments, the parameter is time to peak. According to these embodiments, a longer time to peak is indicative of HCC.

In yet additional specific embodiments, the at least one parameter is one or more PDR values (% dose/hr) at selected time points. According to these embodiments, a decreased PDR value at a selected time point is indicative of HCC.

In some specific embodiments, the at least one parameter is one or more CPDR values at selected time points. According to these embodiments, a decreased CPDR value at a selected time point is indicative of HCC.

In some specific embodiments, the at least one parameter is one or more DOB values at selected time points. According to these embodiments, a decreased DOB value at a selected time point is indicative of HCC.

In some typical embodiments, the labeled octanoate is administered orally. In other embodiments it is administered intravenously or intra nasally.

In some typical embodiments, the labeled octanoate is administered in a predetermined, single dose (e.g. 100 mg for each patient). In other embodiments it is administered based on the patient's body weight (e.g. 2 mg per kilogram).

In some embodiments, the method is adapted for follow-up and monitoring response to HCC treatment in a subject.

In some embodiments, the method comprises performing a first evaluation of the liver function by monitoring an isotope-labeled metabolic product of octanoate in exhaled breath of the subject following a first administration of an isotope-labeled octanoate, and performing a second evaluation of the liver function after a predetermined period of time by monitoring an isotope-labeled metabolic product of octanoate in exhaled breath of the subject following a second administration of an isotope-labeled octanoate.

In some embodiments, the step of performing a second evaluation after a predetermined period of time is repeated a multiplicity of times.

It is to be understood that the terms "a first evaluation of the liver function" and "a second evaluation of the liver function" are not limited to the initial evaluation session and the consecutive session thereafter, but may relate to any two separate evaluation sessions.

As used herein, "decreased", "significantly decreased" or a "significant difference", typically refers to a statistically significant difference, as can be defined by standard methods known in the art.

In some embodiments, reference octanoate metabolism refers to a control octanoate metabolism, as determined in control subjects not afflicted with HCC. In some embodiments, the control subjects have at least one chronic liver disease without HCC. In some exemplary embodiments, the control subjects are cirrhotic patients without HCC. In other embodiments, the control subjects are healthy individuals with no liver diseases.

In other embodiments, reference octanoate metabolism refers to octanoate metabolism determined during a first evaluation of the liver function, e.g., octanoate metabolism previously measured in a tested subject. For example, if the method of the present invention is used for monitoring a response to treatment, breath test results obtained in a first measurement from a particular subject may be used as reference for breath test results obtained in a second measurement from the same subject. For example, a first measurement may be performed before the beginning of treatment and a second measurement may be performed following a predetermined period of time after treatment. In this case, an increased octanoate breath test values in the second measurement in comparison to the first measurement are indicative of positive response to treatment.

In some typical embodiments, the tested subject is a mammal, preferably a human.

In some embodiments, the tested subject is selected from the group consisting of a subject who is at risk of developing HCC, a subject who is suspected of having HCC, and a subject who is afflicted with HCC. Each possibility represents a separate embodiment of the invention.

In some embodiments, the subject is afflicted with HCC and has undergone or is undergoing treatment. Each possibility represents a separate embodiment of the invention.

In some embodiments, the treatment is selected from the group consisting of TACE and RFA or any other drug for HCC including any type of tyrosine kinase inhibitors, and type of chemotherapeutic agent including but not limited to Adriamycin, and any type of immunotherapy used for HCC including but not limited to pulsed dendritic cells, as well as any combination of treatment. This also includes a follow up of response for any adjuvant treatment in patients undergoing surgical resection or liver transplantation. Each possibility represents a separate embodiment of the invention.

In some embodiments, the tested subject has at least one chronic liver disease. In some embodiments, the chronic liver disease is selected from the group consisting of non-alcoholic steatohepatitis (NASH), non-alcoholic fatty liver disease (NAFLD), hepatitis B, hepatitis C or patients with cirrhosis due to any etiology. In general, the disease may be any other type of chronic liver disease with or without cirrhosis, including patients with idiopathic cirrhosis, exposing the patient to primary liver cancer and/or to metastasis. Each possibility represents a separate embodiment of the invention.

In some embodiments, the chronic liver disease is selected from the group consisting of NASH and NAFLD. Each possibility represents a separate embodiment of the invention. According to these embodiments, the method further comprises normalization of the OBT values. NASH/NAFLD are known to affect the liver mitochondrial function (see, for example, Grattagliano I. et al., $^{13}$C-breath tests for clinical investigation of liver mitochondrial function; Eur J Clin Invest 2010; 40 (9): 843-850). In some embodiments, an algorithm is used to correct the values of NASH/NAFLD patients. In some embodiments, different cut-off values are determined for subjects with NASH/NAFLD.

In some embodiments, the tested subject has a liver disease other than NASH. In some embodiments, the tested subject has a liver disease other than NAFLD. In some embodiments, subjects having a liver disease selected from the group consisting of NASH and NAFLD are excluded from being tested using the methods of the present invention.

In some embodiments, the tested subject is treated with sorafenib (which is known to enhance mitochondrial function). According to these embodiments, the method further comprises normalization of the OBT values. In some embodiments, an algorithm is used to correct the values of sorafenib-treated patients. In some embodiments, different cut-off values are determined for subjects treated with sorafenib.

This may also apply to any other type of therapy including any chemotherapy radiotherapy and adjuvant therapy, immunotherapy or inhibitors of intracellular mechanisms, or combination of the above.

In other embodiments, the subject is not treated with sorafenib or any other cancer drug. In some embodiments, subjects treated with sorafenib or any other cancer drug are excluded from being tested using the methods of the present invention.

Thus, in some embodiments, the method further comprises normalization of the values obtained in step (i) according to disease etiology. In additional or alternative embodiments, the method further comprises normalization of the values obtained in step (i) according to a treatment.

In some embodiments, the method further comprises concomitant monitoring of total $CO_2$ in breath, for example, by capnography. This may enable minimizing test length and variations in metabolic rate and/or $CO_2$ production that would introduce non-relevant variables to liver test evaluation.

These and further aspects and features of the present invention will become apparent from the figures, the detailed description, examples and claims which follow.

DETAILED DESCRIPTION OF THE INVENTION

Figure 1:
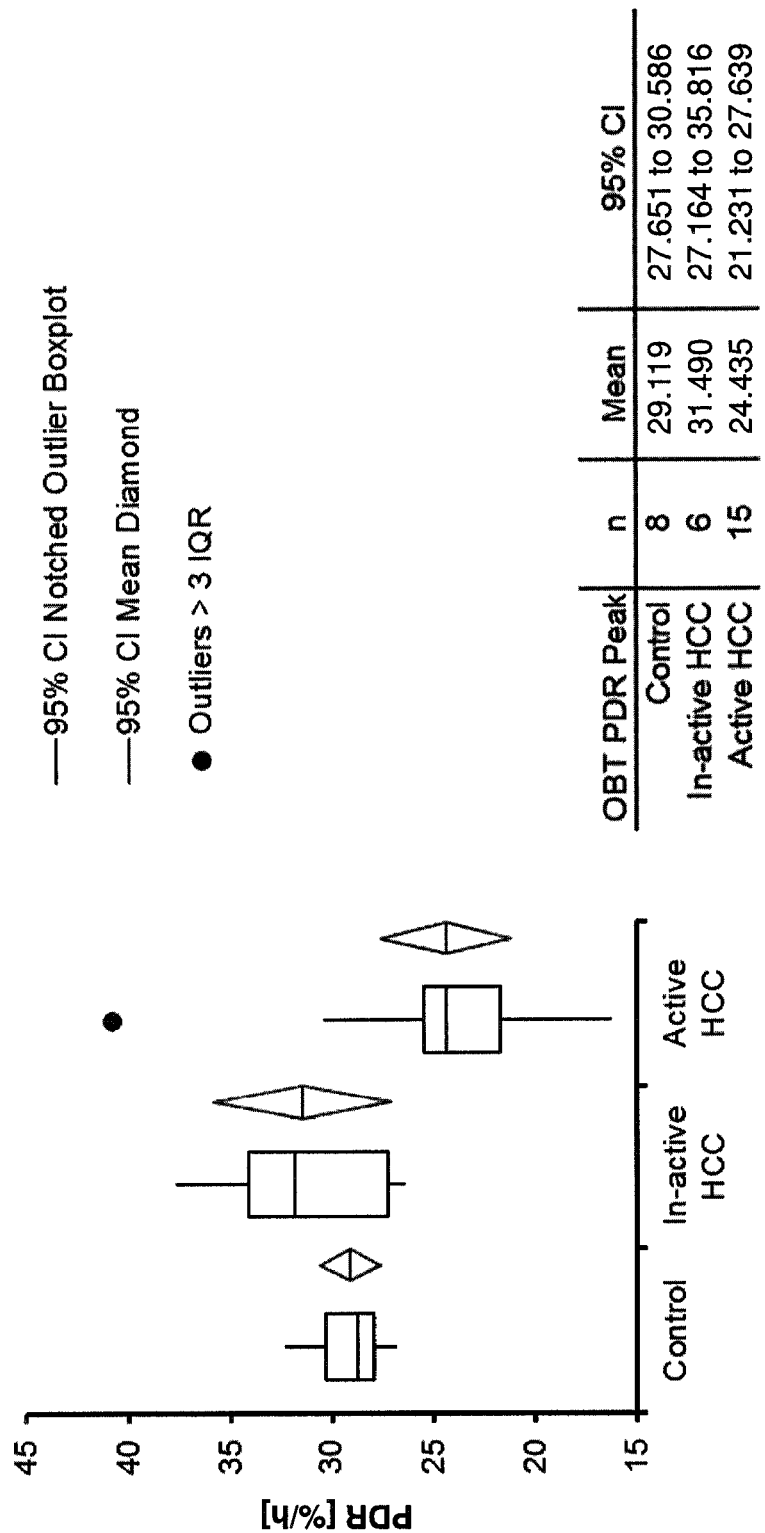
FIG. 1. Boxplot diagram and mean diamond representation of $^{13}$C-octanoate breath test values in active vs. inactive HCC and control.

The present invention is directed to the use of isotope-labeled octanoate or salts or derivatives thereof for the diagnosis, prognosis and follow-up of HCC.

The methods and systems of the present invention effectively differentiate subjects with active HCC from subjects with inactive HCC or with no HCC. Thus, the methods and systems of the present invention are useful for detecting, diagnosing and monitoring HCC in a subject. The methods and systems of the present invention may also be useful for HCC screening, detection of tumor progression, recurrence, prognosis and staging. The methods of the present invention may also be useful for evaluating tumor size and response to any type of therapy. The methods of the present invention may also be useful for detecting HCC recurrence.

The methods of the present invention are based on analysis of breath test parameters. Known quantities of an isotope-labeled exogenous substrate, namely isotope-labeled octanoate, are administered to a subject, and metabolism of the labeled substrate is quantitatively and qualitatively followed. The obtained breath test parameters are compared to reference data. The obtained parameters are indicative of HCC status in the subject. Breath tests according to embodiments of the present invention are based on detecting the isotope-labeled metabolic product in a subject's breath and measuring the ratio between labeled and unlabeled metabolic product. The data may be further processed, for example, by calculating the rate of exhalation of the labeled metabolic product and generating a PDR curve.

Despite the difficulty in evaluating liver condition in breath tests, correlation was observed between the level of octanoate metabolism and the status of HCC in a subject.

According to one aspect, the present invention provides a method for early detection, prognosis and follow-up of HCC in a subject, the method comprising:
(i) determining octanoate metabolism in the subject by monitoring an isotope-labeled metabolic product of octanoate in exhaled breath sample of the subject following administration of an isotope-labeled octanoate; and
(ii) comparing octanoate metabolism in the subject to a reference octanoate metabolism, wherein a significantly decreased octanoate metabolism is indicative of HCC.

In some embodiments, there is provided herein a method for detection, determining the prognosis and/or follow-up of HCC in a subject, the method comprising comparing octanoate metabolism in the subject as determined by monitoring an isotope-labeled metabolic product of octanoate in exhaled breath of the subject following administration of an isotope-labeled octanoate to a reference octanoate metabolism, wherein a significantly decreased octanoate metabolism is indicative of active HCC.

In cirrhotic patients, overall liver function is impaired. The metabolism of KICA, which is used in the prior art, is known to be affected by the overall liver function, and impairment due to cirrhosis affecting KICA breath test values and reducing them in comparison to normal values in subjects with no cirrhosis. However, it is known that some of the HCC patients are not cirrhotic. It is therefore expected that a patient without cirrhosis, but with HCC cannot be efficiently detected by KICA. Advantageously, the method according to embodiments of the present invention utilizes a compound whose metabolism is unaffected by overall liver function. The OBT peak values are similar for healthy, controls with cirrhosis or subjects with inactive HCC versus the subjects with HCC (independent of their actual liver impairment). It is therefore expected that a patient without cirrhosis, but with HCC can be detected by octanoate breath test.

Typically, an isotope-labeled octanoate is administered to the subject, and breath sample(s) are collected. In some embodiments, monitoring is performed by continuous measurement over a predetermined period of time. In some embodiments, a continuous measurement is performed using, for example, a Breath ID® System (Exalenz Bioscience Ltd.). Such measurement enables accurate assessment of the PDR peak, which is currently a preferred indicative measure for the presence of HCC, and may be used for early detection of small tumors.

In other embodiments, monitoring is performed by collecting a plurality of breath samples from the subject at periodic intervals or at defined time points over a predetermined period of time following a single administration of a labeled octanoate, and measuring the isotope ratio in said samples.

In some embodiments, samples are collected by continuous on-line sampling.

In some embodiments, the predetermined period of time ranges from about 0.1-1 hour, from about 0.1-2 hours, from about 0.1-3 hours, from about 1-2 hours, from about 1-3 hours, from about 1-4 hours, from about 2-4 hours. Each possibility represents a separate embodiment of the invention.

In some embodiments, a periodic interval for the collection of breath samples ranges from about 0.5-30 min, from about 10-30 min, from about 20-60 min, from about 30-60 min. Each possibility represents a separate embodiment of the invention.

In some embodiments, monitoring begins only after administration of the labeled substrate. In other embodiments, monitoring begins before the labeled substrate is administered. In some embodiments, a baseline reading or baseline values are generated.

In some embodiments, the exhaled isotope-labeled metabolic product is measured in at least three time points, for example, to generate a percentage dose recovery (PDR) curve. The metabolic activity may be determined from the PDR.

In some embodiments, the method includes on-line monitoring a metabolic product of octanoate in a subject's breath after administering to the subject isotope-labeled octanoate.

In some typical embodiments, the metabolic product is $CO_2$. In some embodiments, the isotope is selected from the group consisting of carbon-13, carbon-14 and oxygen-18. In some typical embodiments, the isotope is $^{13}C$. For example, hepatic metabolism of $^{13}C$-octanoate may be assessed by measuring the ratio of $^{13}C/^{12}C$ in exhaled breath. Carbon-13 is a stable, non-radioactive isotope, which can be incorporated into a specific location within the molecule of a test substrate so that after its metabolism by the liver and generation of $^{13}CO_2$, it would be released. The $^{13}C$-compound may be administered orally, rapidly absorbed and metabolized by the liver, and then the $^{13}CO_2$ may be measured in exhaled breath within a predetermined period of time.

In some embodiments, monitoring comprises generating at least one of percentage dose recovery (PDR) curve, cumulative percentage dose recovery (CPDR) curve and delta over baseline (DOB) curve, and calculating at least one parameter of said PDR, CPDR and DOB curve.

In some embodiments, comparing comprises comparing the calculated at least one parameter to at least one parameter of reference PDR, CPDR and DOB curves.

In some embodiments, comparing octanoate metabolism in the subject to a reference octanoate metabolism comprises generating a percentage dose recovery (PDR) curve for the subject and comparing at least one parameter of said PDR curve to at least one parameter of a reference PDR curve. PDR curves are known in the art. Such curves depict the rate of metabolism of the labeled substrate in % dose/hour (percentage of the administered dose recovered per hour), as measured in breath. PDR curves reflect dynamic response of the liver.

In some embodiments, the at least one parameter is selected from the group consisting of peak height, time of appearance of the peak and the slope of rate of metabolism. Each possibility represents a separate embodiment of the invention. In alternative or additional embodiments, the parameter is one or more PDR values (% dose/hr) at selected time points.

In some embodiments, comparing octanoate metabolism in the subject to a reference octanoate metabolism comprises generating a cumulative percentage dose recovery (CPDR) curve for the subject and comparing at least one parameter of said CPDR curve to at least one parameter of a reference CPDR curve. CPDR curves are known in the art. Such curves depict the amount of the labeled substrate that was metabolized in % dose (cumulative percentage of the administered dose recovered over time), as measured in breath. The cumulative recovery of labeled $CO_2$ in breath can be calculated as the area under the curve (AUC) of PDR.

In some embodiments, the parameter is one or more CPDR values at selected time points, for example, CPDR values at 30, 40 and/or 45 minutes.

In some embodiments, comparing octanoate metabolism in the subject to a reference octanoate metabolism comprises generating a delta over baseline (DOB) curve and comparing at least one parameter of said DOB curve to at least one parameter of a reference DOB curve. DOB curves are known in the art. Such curves depict the difference between the isotope ratio (for example, $^{13}CO_2/^{12}C_2$) in a test sample collected at a certain time point and the corresponding ratio in a baseline sample.

In some embodiments, the parameter is one or more DOB values at selected time points.

PDR curves represent normalization of the DOB per subject taking into consideration the subject's $CO_2$ production rate based on height and weight and the amount of substrate administered. In some embodiments, the subject is administered a dosage of Octanoate based on the subject's weight (e.g. 1 mg or 2 mg or 3 mg per kilo), According to these embodiments, DOB curves are more preferred for analysis. In other embodiments, the subject is administered a fixed, predetermined dose of octanoate (e.g., 100 mg). According to these embodiments, PDR curves are more preferred for analysis.

Typically, the selection of breath test parameters for analysis according to embodiments of the present invention deals with extra-hepatic metabolism or overcomes the problem of extra-hepatic metabolism. Generally, analysis is performed for information obtained only until a peak is detected, for example—peak height and peak time.

In some specific embodiments, the parameter is peak height. According to these embodiments, a decreased peak height is indicative of HCC.

In some typical embodiments, the labeled octanoate is administered orally, intravenously or intra-nasally.

In some embodiments, the method is adapted for follow-up and monitoring response to HCC treatment in a subject. In some embodiments, the method comprises performing a first evaluation of the liver function by monitoring an isotope-labeled metabolic product of octanoate in exhaled breath of the subject following administration of an isotope-labeled octanoate, and performing a second evaluation, after a predetermined period of time, of the liver function by monitoring an isotope-labeled metabolic product of octanoate in exhaled breath of the subject. In some embodiments, the step of performing a second evaluation, after a predetermined period of time, is repeated a multiplicity of times.

The term "multiplicity" may refer to any number higher than 1. In some embodiment, the term "multiplicity" refers to any number higher than 2. In other embodiments, the term "multiplicity" refers to any number higher than 3.

As used herein, "decreased", "significantly decreased" or a "significant difference", typically refers to a statistically significant difference, as can be defined by standard methods known in the art.

Typically, control octanoate metabolism is determined in subjects not afflicted with HCC. In some embodiments, the control subjects have at least one chronic liver disease without HCC. In some exemplary embodiments, the control subjects are cirrhotic patients without HCC. In other embodiments, the control subjects are healthy individuals with no liver diseases.

Control octanoate metabolism, according to the principles of the present invention, is determined in at least one subject, preferably a plurality of subjects. A set of control parameters determined in control subjects may be stored as a reference collection of data.

In some typical embodiments, the tested subject is a mammal, preferably a human.

In some embodiments, the tested subject is selected from the group consisting of a subject who is at risk of developing HCC, a subject who is suspected of having HCC, and a subject who is afflicted with HCC. Each possibility represents a separate embodiment of the invention.

In some embodiments, the subject is afflicted with HCC and has undergone or is undergoing treatment. Each possibility represents a separate embodiment of the invention. In some embodiments, the treatment is selected from the group consisting of TACE and RFA or any other drug for HCC including any type of tyrosine kinase inhibitors, and type of chemotherapeutic agent including but not limited to Adriamycin, and any type of immunetherapy used for HCC including but not limited to pulsed dendritic cells, as well as any combination of treatment. This also includes a follow up of response for any adjuvant treatment in patients undergoing surgical resection or liver transplantation. Each possibility represents a separate embodiment of the invention.

In some embodiments, the method further comprises normalization of the values obtained in step (i) according to disease etiology. In some embodiments, the disease etiology is selected from the group consisting of NASH and NAFLD.

In alternative or additional embodiments, the method further comprises normalization of the values obtained in step (i) according to one or more blood test results. In some embodiments, the one or more blood tests are selected from the group consisting of fasting glucose levels, insulin levels, ALT levels, AST levels, ALP levels, GGTP levels, bilirubin levels, albumin levels and sodium levels.

In alternative or additional embodiments, the method further comprises normalization of the values obtained in step (i) according to an HCC treatment that the subject is receiving or has received. In some embodiments, the treatment is sorafenib administration.

In some embodiments, the exhaled isotope-labeled metabolic product is measured spectroscopically, for example, by infrared spectroscopy, or with a mass analyzer.

In some embodiments, monitoring the isotope-labeled metabolic product of octanoate in exhaled breath of a subject comprises the use of at least one technique selected from the group consisting of gas-chromatography (GC), GC-lined mass-spectrometry (GC-MS), proton transfer reaction mass-spectrometry (PTR-MS), electronic nose device, and quartz crystal microbalance (QCM). Each possibility represents a separate embodiment of the invention.

In some embodiments, the tested subject has at least one chronic liver disease. In some embodiments, the chronic liver disease is selected from the group consisting of non-alcoholic steatohepatitis (NASH), non-alcoholic fatty liver disease (NAFLD), hepatitis B and hepatitis C or any other type of chronic liver disease with or without cirrhosis exposing the patient to primary liver cancer and/or to metastasis. Each possibility represents a separate embodiment of the invention.

In some embodiments, the chronic liver disease is selected from the group consisting of NASH and NAFLD. Each possibility represents a separate embodiment of the invention. According to these embodiments, the method further comprises normalization of the OBT values. NASH/NAFLD are known to affect the liver mitochondrial function (see, for example, Grattagliano I. at al. $^{13}$C-breath tests for clinical investigation of liver mitochondrial function; Eur J Clin Invest 2010; 40 (9): 843-850).

In some embodiments, an algorithm and/or a different cut-off is used to correct the values of NASH/NAFLD patients. A suitable algorithm may include certain blood test results that represent the disease severity of those patients, including, but not limited to, fasting glucose levels, insulin levels and/or liver panel (e.g. ALT, AST, ALP, GGTP, Bilirubin, Albumin, Sodium levels).

In some embodiments, the tested subject has a liver disease other than NASH/NAFLD.

In some embodiments, the tested subject is treated with sorafenib (enhancing mitochondrial function). According to these embodiments, the method further comprises normalization of the OBT values and/or use of a different cut-off. In some embodiments, an algorithm is used to correct the values of sorafenib-treated patients. For example, the breath test results may be normalized as a function of the sorafenib dosage, frequency, and time of therapy already completed.

This may also apply to any other type of therapy including any chemotherapy radiotherapy and adjuvant therapy, immunotherapy or inhibitors of intracellular mechanisms, or combination of the above. In other embodiments, the subject is other than a subject treated with sorafenib, The method may further include monitoring total $CO_2$ in breath. $CO_2$ may be monitored, for example, by capnography. This may minimize test length and variations in metabolic rate and/or $CO_2$ production that would introduce non-relevant variables to the HCC evaluation.

The method may further include analyzing at least one breath related parameter obtained by monitoring the metabolic product of octanoate in combination with at least one breath related parameter obtained by monitoring total $CO_2$ in breath. The method may further include analyzing at least one breath related parameter obtained by monitoring the metabolic product of octanoate in combination with at least one physiological and/or medical parameter. The physiological and/or medical parameter may include age, gender, weight, height, blood related parameter, body mass index (BMI), waist circumference, medication therapy related parameter, background diseases or any combination thereof. Each possibility represents a separate embodiment of the invention.

In some embodiments, the octanoate breath test results are combined with demographic and clinical data of the subject to generate a prediction score.

In some embodiments, demographic parameters are also considered and evaluated.

In some embodiments, the method further comprises computing an hepatic impairment score (HIS) based at least on a breath test related parameter and on a demographic parameter.

Non-limiting examples of demographic parameters include height, weight, age, gender, smoking habits, disease etiology, known information about complications, or any combination thereof. The demographic information can be used to:
(i) compensate for inter-patient factors that affect a breath test; and/or
(ii) deal with factors that affect disease and that, together with breath test data, may allow provision of a reliable predication of disease severity and/or status. The information may relate to any one or more items from the following list (and/or to any other relevant information): height and weight, age, gender, smoking habits, disease etiology, known information about complications (including but not limited to, shunts, portal hypertension, encephalopathy, varices, variceal bleeding, abnormal blood test such as bilirubin, edema and/or ascites, decompensated cirrhosis, consumption of certain drugs that may impact the metabolic path of octanoate) and common scores that assess liver disease severity such as the Child-Turcotte-Pugh (CTP), Model for Endstage Liver Disease (MELD) and/or Sodium MELD (Na-MELD) scores.

Information about computing an HIS score can be found in International Patent Application Publication No. WO 2010/013235.

In general, detecting, monitoring, distinguishing, evaluating, measuring, differentiating, quantifying, and the like as referred to herein may be accomplished by any of the apparatuses, breath collection systems, analyzer units, calibration devices, algorithms and methods described herein, and/or, as non-limiting examples, by any of the apparatuses, breath collection systems, analyzer units, calibration devices, algorithms and methods disclosed in U.S. Pat. Nos. 6,186,958, 6,491,643 and 6,656,127; and U.S Patent Application Publication Nos. 2003/0216660 and 2001/0021815.

Additional non-limiting examples of devices suitable for the methods of the present invention are those described in International Patent Application Publication Nos. WO 2007/054940 and WO 2010/013235.

Typically, a device suitable for the methods of the present invention comprises a breath test analyzer, including a very sensitive gas analyzer, capable of measuring a ratio of two chemically identical gases with different molecular weights. The gas analyzer is capable of measuring small quantities of isotopically labeled gas, which may be present in the breath of a subject.

In some embodiments, there are at least two modes of analyzing the breath samples. The analyzer can either perform its analysis on individual exhaled breaths, or it can perform its analysis on-line on multiple samples of the patient's breath, continuously collected from the patient.

In some embodiments, the breath test analyzer includes a breath analysis chamber, a breath inlet conduit for conveying exhaled gas from a patient to the breath analysis chamber; and a gas analyzer operative to analyze gas in the breath analysis chamber and to conduct the first analyzing of gas exhaled by the patient.

In some embodiments, monitoring an isotope-labeled metabolic product of octanoate is performed by continuous measurement. In some embodiments, on-line monitoring is performed, in real time, whilst a subject is continuing to provide breath for subsequent analyses. Suitable devices for on-line monitoring may include, for example, one or more breath sensors adapted to monitor an isotope level within a metabolic product of labeled octanoate, or a salt or a derivative of octanoate, and a controller adapted to on-line sample measurements of the one or more sensors at a continuous mode.

The device may be adapted to sample measurements of the one or more sensors at a continuous mode, while the subject is coupled to the device during breath sampling, for example, through a nasal cannula. The device may be adapted to automatically collect and analyze breath samples.

The device may further include one or more breath sensors, such as capnography sensors, adapted to monitor $CO_2$ in breath.

The device may further include a processor adapted to analyze at least one breath related parameter obtained by monitoring isotope level within a metabolic product of a labeled substance, such as octanoate, in combination with at least one breath related parameter obtained by monitoring $CO_2$ in breath. The processor may correct for changes in $CO_2$ exhaled/production of a subject throughout the breath test.

In some embodiments, a portable office-based system may continuously sense and collect exhaled breath and analyzes $CO_2$ in on-line in real-time through a nasal cannula worn by the subject, and may enable evaluation of HCC status in real time, thereby providing a follow-up method in clinical hepatology. In some embodiments, such a test is designed to provide a sensitivity and accuracy required for accurate detection of clinically relevant variations as small as $1/1000$ in the $^{13}CO_2/^{12}CO_2$ ratio.

In some embodiments, breath tests according to embodiments of the present invention are performed at the point-of-care.

Without wishing to be bound by any theory or mechanism of action, in some embodiments, the decrease in OBT in patients with active HCC, even for the ones smaller than 2 cm, may reflect either a factor or factors secreted by the tumor cells that is affecting the overall mitochondrial function in these patients.

In some embodiments, any type of therapy that counteracts this putative factor or factors, may have an effect on alleviation of the malignant process.

Without wishing to be bound by any theory or mechanism of action, in some embodiments, there is trapping of the octanoate in the tumor either due to its hypervascularity or within the tumor cells or in between the cells.

In some embodiments, both mechanisms, trapping of octanoate and factor or factors secreted by the tumor cells may be acting simultaneously.

In some embodiments, the octanoate can be conjugated to a chemotherapeutic agent as a method of delivering the chemotherapy into the tumor, thus preventing or reducing unwanted systemic side effects of the drug, and enabling the use of high concentration of the drug inside the tumor.

In some embodiments, these therapeutic agents also include any type of chemotherapy, radiotherapy including but not limited to radioactive substrates such as iridium, immunotherapies, gene therapy, or any combination of the above. The octanoate can therefore serve as an agent or carrier for delivering the therapy.

In some embodiments, since the octanoate is concentrated in the tumor it can also serve as a tool for imaging, as an effective alternative to currently known agents, e.g. in cases where lipiodol is used in CT or MRI.

The methods of the present invention are based on metabolism of octanoate ($C_8H_{16}O_2$) by liver mitochondria. The metabolism of fatty acids (such as octanoate) and the release of the $^{13}C$-carbon in a form of $^{13}CO_2$ requires multiple steps including beta-oxidation, generation of $^{13}C$ labeled Acetyl-CoenzymeA (AcCoA) and subsequently release of the $^{13}C$ carbon in the tricarboxylic acid (TCA) cycle (also known as the citric acid cycle or the Krebs cycle). Improper TCA function may lead to accumulation of AcCoA. It is known that alternative pathways exist for AcCoA, which result in ketone bodies generation or lipogenesis, which would not be detected in a breath test. The percentage of the labeled octanoate that continues in the TCA cycle versus the percentage of the labeled octanoate that goes to generation of ketone bodies may depend on the physiological condition of the subject. For example, in starving/fasting conditions, oxalacetic acid may be needed (as it is used by the cells in the glucose synthesis/gluconeogenesis) which results in a less effective TCA process. The varying (and sometimes unpredicted) ratio between the amount of labeled octanoate that "takes" the TCA cycle path and the amount of labeled octanoate that "takes" alternative paths may affect the accuracy of the breath test. In some embodiments, the following steps are provided, independently from each other or in any combination, for increasing the diagnostic accuracy of the octanoate breath test:

a. Using low dosage (such as in the range of about 100 mg) of octanoate or octanoate salt to avoid saturation of the TCA cycle. In general, octanoate dosage to be administered may be selected by body weight, e.g., about 1 mg/kg-3 mg/kg, allowing a dosage ranging from about 15 mg (in children with 1 mg/kg) to about 450 mg (in obese patients with 3 mg/kg).

b. Patients may be tested after >8 hours fasting that assure that the metabolic conditions are more or less stable and less sensitive to variations which are due to consuming a meal.

c. The test meal may include glucose and 13C octanoate.

d. The test meal may include aspartame (and 13C octanoate salt), which provides aspartic acid, which is the source of oxalacetic acid.

e. An alternative to c and/or d is wherein glucose/aspartame are administered prior to the test.

f. Using of drugs that block/reduce the ketonic generation path-way (for example, HMG-CoA reductase inhibitors).

g. Measuring ketone bodies generation with biochemical tests (ketonuria and/or plasma serum ketone bodies concentration) in conjunction to the 13C-octanoate breath test to improve diagnostic accuracy of the test.

h. Looking for traces of 13C-octanoate in blood.

According to another aspect, the present invention provides a device for detection, prognosis and/or follow-up of HCC in a subject, the device comprising a processor configured to detect differences between octanoate metabolism in the subject and control octanoate metabolism, wherein a decreased octanoate metabolism is indicative of HCC.

In some embodiments, the processor is configured to monitor an isotope-labeled metabolic product of octanoate in exhaled breath of the subject following administration of an isotope-labeled octanoate, and compare octanoate metabolism in the subject to a reference octanoate metabolism, wherein a significantly decreased octanoate metabolism is indicative of active HCC.

In some embodiments, the processor is adapted to normalize the breath test values according to disease etiology, treatment or a combination thereof.

In some embodiments, the processor is adapted to calculate and generate at least one of DOB curve, PDR curve and CPDR curve, and compare at least one parameter of said DOB, PDR or CPDR at least one reference parameter.

In some embodiments, the at least one parameter is selected from the group consisting of PDR maximum level (peak height), time of appearance of the peak (time to peak) and the slope of rate of metabolism. Each possibility represents a separate embodiment of the invention.

In some embodiments, the processor is further adapted to compute an output indication related to HCC based on the differences in octanoate metabolism.

In some embodiments, the processor is further adapted to compute an output indication related to HCC based on the differences in at least one parameter of DOB, PDR and/or CPDR.

In some embodiments, the processor is further adapted to concomitantly monitor total $CO_2$ in breath.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

13C-Octanoate Breath Test Values in Active Vs. Inactive HCC and Control

Patients with active or inactive HCC (after successful therapy) were recruited. The degree of activity was determined based on injection of contrast media (Lipiodol®) under CT and/or MRI. In addition, cirrhotic patients without any evidence of HCC were also recruited (used as a control group). Information about the study population is provided in Tables 1, 2 and 3 hereinbelow.

TABLE 1

| Gender | Active HCC | Inactive HCC | Control | Grand Total |
| --- | --- | --- | --- | --- |
| F | 4 | 3 | 4 | 11 |
| M | 11 | 3 | 4 | 18 |
| Grand Total | 15 | 6 | 8 | 29 |

TABLE 2

| Etiology | Active HCC | Inactive HCC | Control | Grand Total |
| --- | --- | --- | --- | --- |
| Cryptogenic | 2* | 1 | — | 3 |
| HBV | 2 | 1 | 1 | 4 |
| HCV | 7 | 3 | 6 | 16 |
| NASH | 4 | 1 | — | 5 |
| Sarcoidosis | — | — | 1 | 1 |
| Grand Total | 15 | 6 | 8 | 29 |

*One male patient was on Nexavar™ (sorafenib) treatment before doing OBT.

TABLE 3

| | AFP levels | | | |
| --- | --- | --- | --- | --- |
| HCC Status | Minimum | Maximum | Median | Mean |
| Control | 1.42 | 33.30 | 3.40 | 7.39 |
| Inactive HCC | 4.60 | 31.90 | 6.28 | 12.27 |
| Active HCC | 3.99 | 5990.00 | 57.70 | 652.08 |

All patients have undergone dynamic $^{13}$C-octanoate breath test (OBT) using BreathID® device (Exalenz Bioscience Ltd.) before and/or after treatment. Three male subjects with active HCC, of which two with HCV and one with NASH, were tested twice (one test before treatment and one test after).

The breath tests were performed according to the following procedure:

a. Preparation of the study subject:
   Patients were asked to perform the breath test after an overnight fast (including morning medication). The patients were allowed to drink small amounts of water until 1 hour prior to test. The patients rested for 3-5 minutes prior to the test start (to assure that breathing rate and pulse are normal and constant throughout the test).

b. Preparation of $^{13}$C-Octanaote:
   100 mg of $^{13}$C-Octanoate powder were emptied into a disposable cup and 150 cc of water were added. The mixture was mixed until the substrate has been completely dissolved.
   Just prior to the examination, this solution was poured into a disposable cup.

c. Administration of the breath test:
   i. Each patient was asked to sit in a chair in the room where the test was performed.
   ii. A nasal cannula was attached to a BreathID® device and to the patient.
   iii. The BreathID® device was activated and collected the patient's baseline exhaled $CO_2$ for approximately 2 minutes.
   iv. The patient was then instructed by the medical staff and by an indication on the device to drink the test substrate.
   v. The patient remained seated in the chair, breathing in a normal manner for the next 60 minutes.
   vi. The BreathID® device continuously measures and analyzes the patient's exhaled breath in real time. As the test substrate is metabolized, the value of the $^{13}CO_2/^{12}CO_2$ ratio changes and calculated in real time by the BreathID® system from the exhaled breath. The BreathID® also calculates in real time the percentage dose recovery (PDR), expressed in %/hour and the cumulative PDR(CPDR). These values are displayed on the screen of the BreathID® device as they are calculated in real time.
   vii. If at any time the device does not detect patient's breath, or if there is any other deviation from the desired test requirements, the device produces an appropriate warning signal.
   viii. At the completion of the procedure the nasal cannula was removed and the patient was allowed to leave the testing room.

The patient was under the supervision of the physician or any other qualified medical staff during the entire test.

For each breath test, a percentage dose recovery (PDR) and cumulative PDR(CPDR) curves were generated. The PDR peak values were grouped according to active/inactive HCC and control, and presented in a boxplot diagram. Mean diamond representation was also generated. The results are shown in FIG. 1.

The data was entered into a validated excel sheet and analyzed with the Analyze-It® Software version 2.12.

Figure 2:
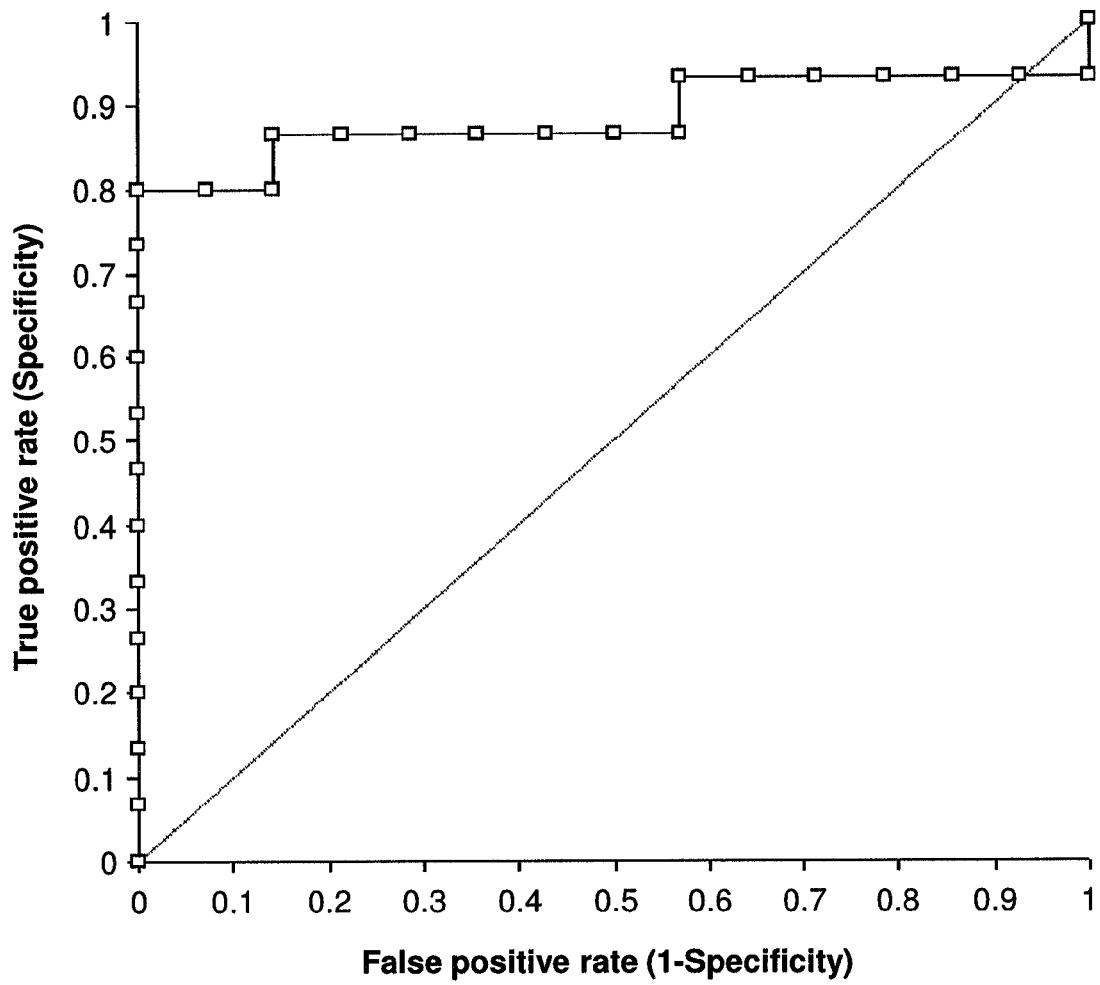
FIG. 2. ROC curve of $^{13}$C-octanoate breath test values in active vs. inactive HCC and control.

In addition, a receiver operating characteristic (ROC) curve was generated (FIG. 2) and $AUC_{ROC}$ was calculated in order to asses the predictive value of the PDR peak in discriminating between active and inactive HCC or control. An $AUC_{ROC}$ value of 0.89 (95% Cl 0.74-1.00, p<0.0001) was obtained.

Figure 3:
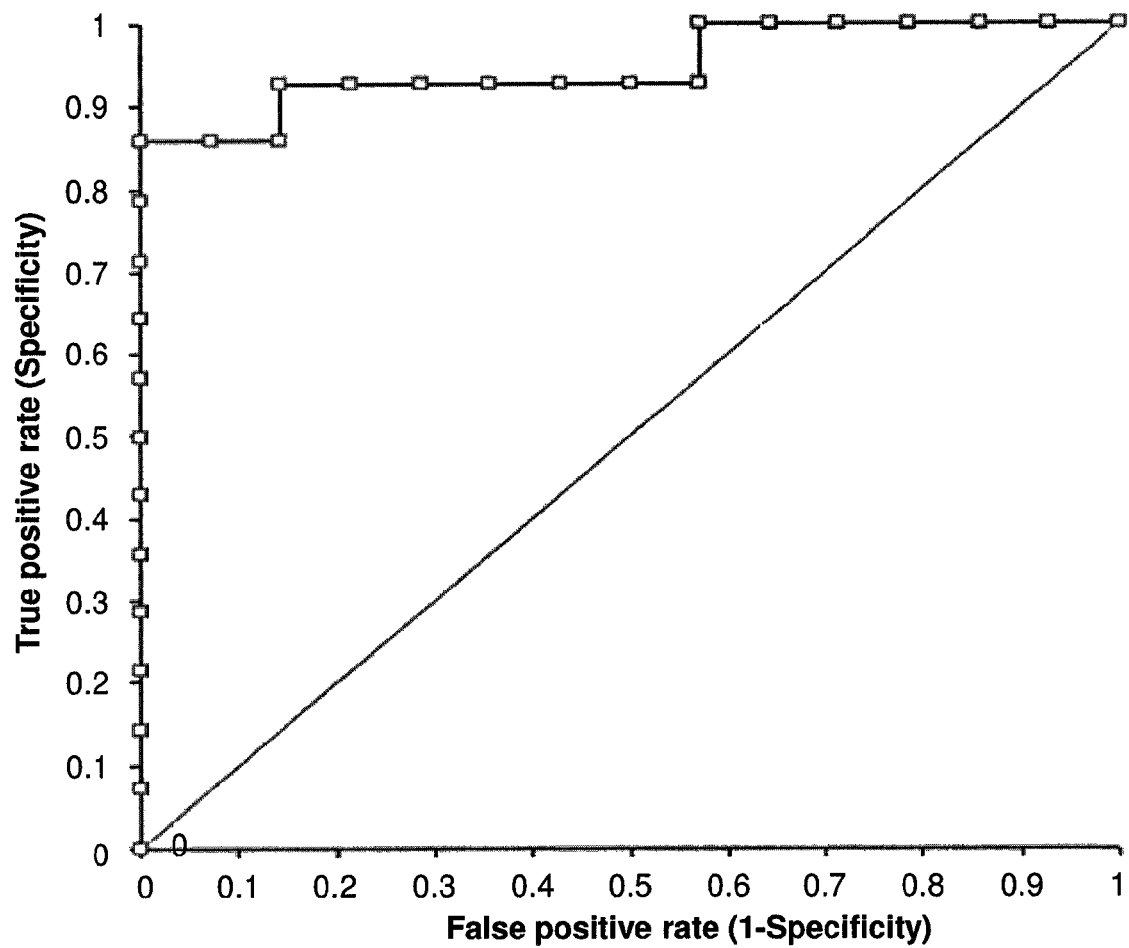
FIG. 3. ROC curve of $^{13}$C-octanoate breath test values in active vs. inactive HCC and control, excluding a sorafenib-treated patient.

The outlier of the boxplot diagram (in FIG. 1) corresponds to a sample obtained from a patient that was treated with sorafenib due to the presence of HCC and prior to the OBT tests. Previous studies (see, for example, Kuroso et al. (2009) Cancer Res. 69:3927-3936) have shown that sorafenib can improve mitochondrial function. Accordingly, OBT values are expected to be higher in HCC patients treated with sorafenib. A second analysis of the results was performed, this time without the sample obtained from the sorafenib-treated patient. The ROC curve is shown in FIG. 3 showing an $AUC_{ROC}$ value of 0.95 (95% Cl 0.86-1.00, p<0.0001).

Figure 4:
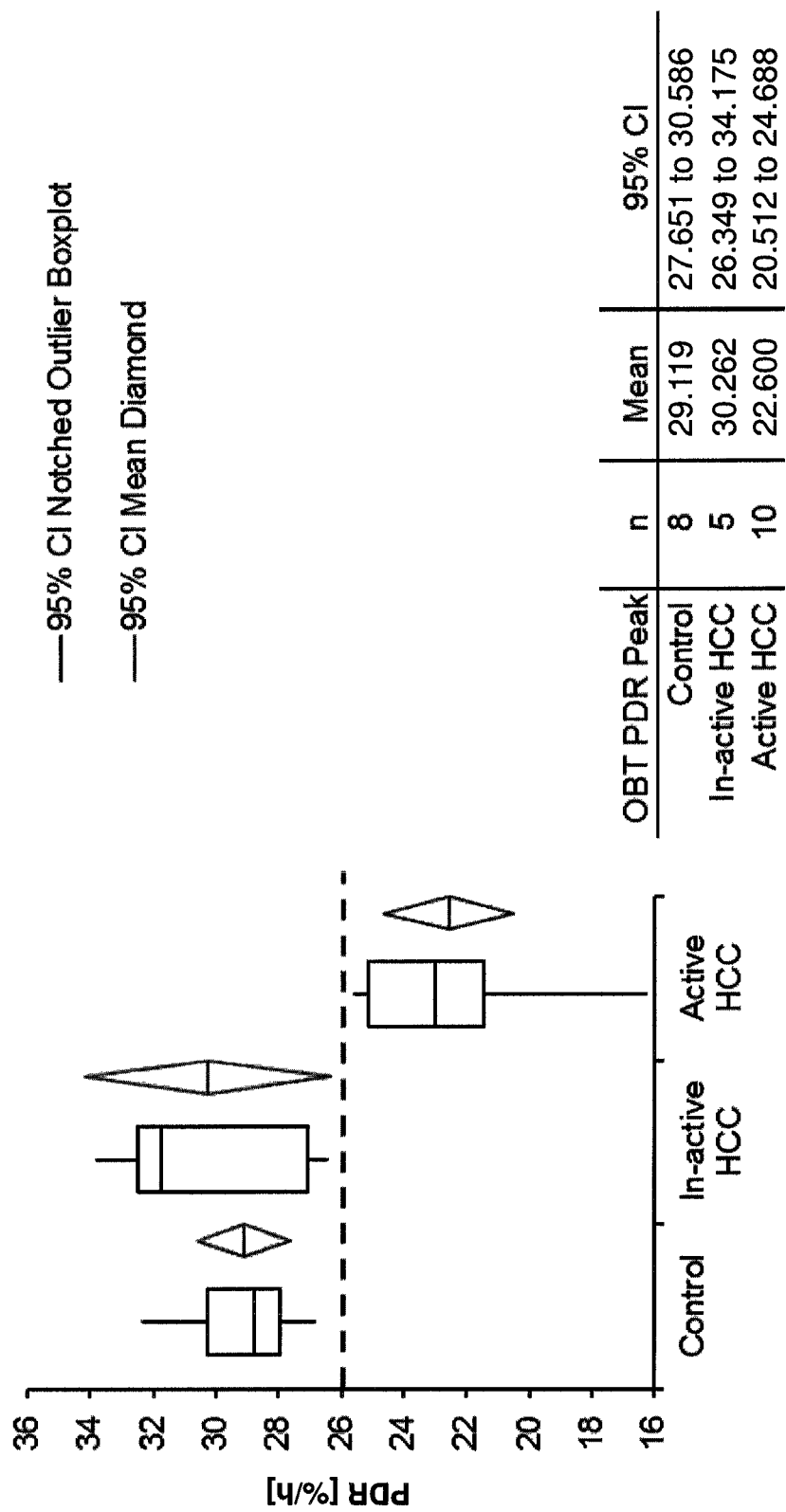
FIG. 4. Boxplot diagram and mean diamond representation of $^{13}$C-octanoate breath test values in active vs. inactive HCC and control, excluding NASH subjects with HCC and a sorafenib-treated patient.

It is known from previous studies that the presence of NASH enhances OBT values (see for example, Braun M et al. "The unique breath ID test system diagnoses and predicts the extent of hepatic injury in patients with nonalcoholic fatty liver disease", Hepatology, 2005; 42: 752A.). Indeed, in the present study the samples of two NASH subjects with HCC had elevated OBT results. A third analysis was performed, this time without the samples obtained from the NASH subjects with HCC and without the patient treated with sorafenib. The boxplot was regenerated from this cleaner sample (see FIG. 4). The ROC analysis has shown an $AUC_{ROC}$ value of 1 (p<0.0001), meaning that full discrimination between active and inactive HCC or control can be obtained when analyzing the dataset without NASH and sorafenib treated subjects. This observation suggests that for diagnostic purposes the etiology should be included (e.g. with or w/o NASH). Suggested cutoff w/o NASH is Peak 26%/h (see dashed line in FIG. 4).

As noted above, three male subjects (two with HCV and one with NASH) were tested twice (once before treatment and once after). Breath test values of these subjects showed full agreement between OBT and patient status:

Subject 01—with successful treatment
First visit showed OBT peak=16.30 %/h
Second visit 3 months after TACE showed OBT peak=31.78 %/h
HCC became inactive following TACE (AFP was 5.84 and 5.48 ng/mL respectively, demonstrating the sensitivity limitations of AFP measurements. Typically, AFP values above 10 ng/mL are considered abnormal. Changes within the normal limits (9 and below) cannot be determined and evaluated accurately).
Subject 02—HCC remained active after TACE
First visit showed OBT peak=25.36 %/h
Second visit 3 months after TACE OBT peak=22.19 %/h
Clinically patient deteriorated and AFP increased from 3500 to 4800 ng/mL.
Subject 05—NASH patient with successful treatment after TACE
First visit showed OBT peak=30.35 %/h
Second visit 5 months after TACE OBT peak=37.63 %/h
Clinically patient improved and CT showed inactive HCC.

It was observed that the activity of HCC can be also determined for the treatment follow-up. The NASH subjects may have another threshold to determine the activity status of HCC, however the OBT Peak improved in NASH patient after successful treatment.

A summary of OBT performance parameters obtained from different analyses is provided in Table 4 hereinbelow.

TABLE 4

| Populations | N | AUC | CI | P-value |
| --- | --- | --- | --- | --- |
| All (active/inactive + control) | 29 (15/14) | 0.89 | 0.74-1.00 | <0.001 |
| Active/inactive | 21 (15/6) | 0.90 | 0.76-1.00 | <0.001 |
| Active/control | 23 (15/8) | 0.88 | 0.72-1.00 | <0.001 |
| All w/o Nexavar™ | 28 (14/14) | 0.95 | 0.86-1.00 | <0.001 |
| All w/o Nexavar™ and NASH | 23 (10/13) | 1.00 | NA | NA |

As mentioned above an $AUC_{ROC}$ value of 1 (p<0.0001), indicating full discrimination between active HCC and inactive HCC+ control, was obtained when the dataset was analyzed without Nexavar™ and without NASH.

Example 2

PDR Curves

Additional $^{13}C$-octanoate breath tests (OBT) were carried out and their results are shown in FIGS. 5-9. The tests were performed according to the procedure described in Example 1 above.

Figure 5:
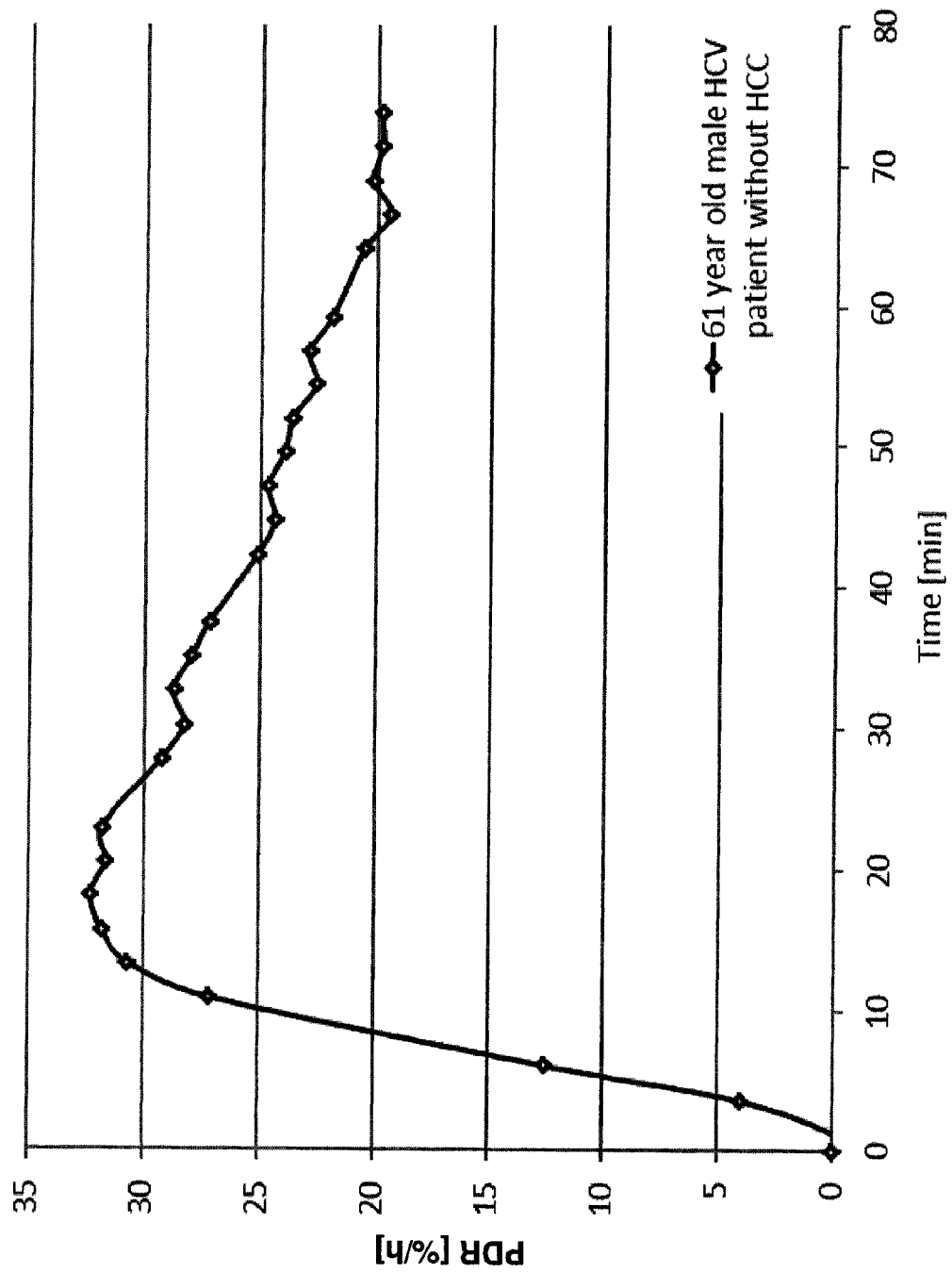
FIG. 5. PDR curve of $^{13}$C-octanoate breath test of a 61 year old male HCV patient without HCC.

FIG. 5 shows an OBT PDR curve of a typical cirrhotic patient without liver cancer. The PDR peak is reached within 30 minutes and is relatively high (~30 %/h).

Figure 6:
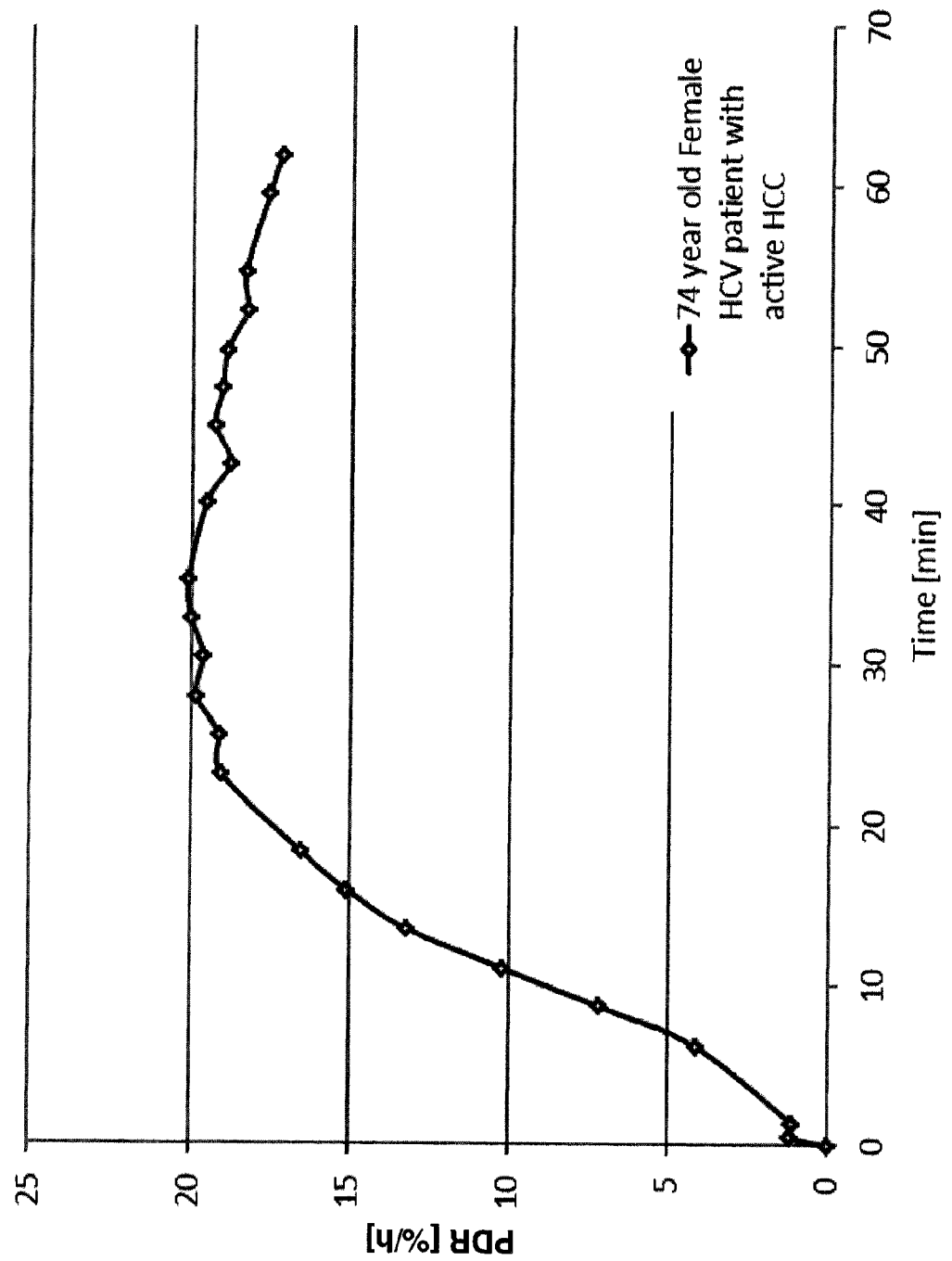
FIG. 6. PDR curve of $^{13}$C-octanoate breath test of a 74 year old female HCV patient with active HCC.

FIG. 6 shows an OBT PDR curve of a typical cirrhotic patient with liver cancer. The PDR peak is delayed (after 30 minutes) and is typically low.

Figure 7:
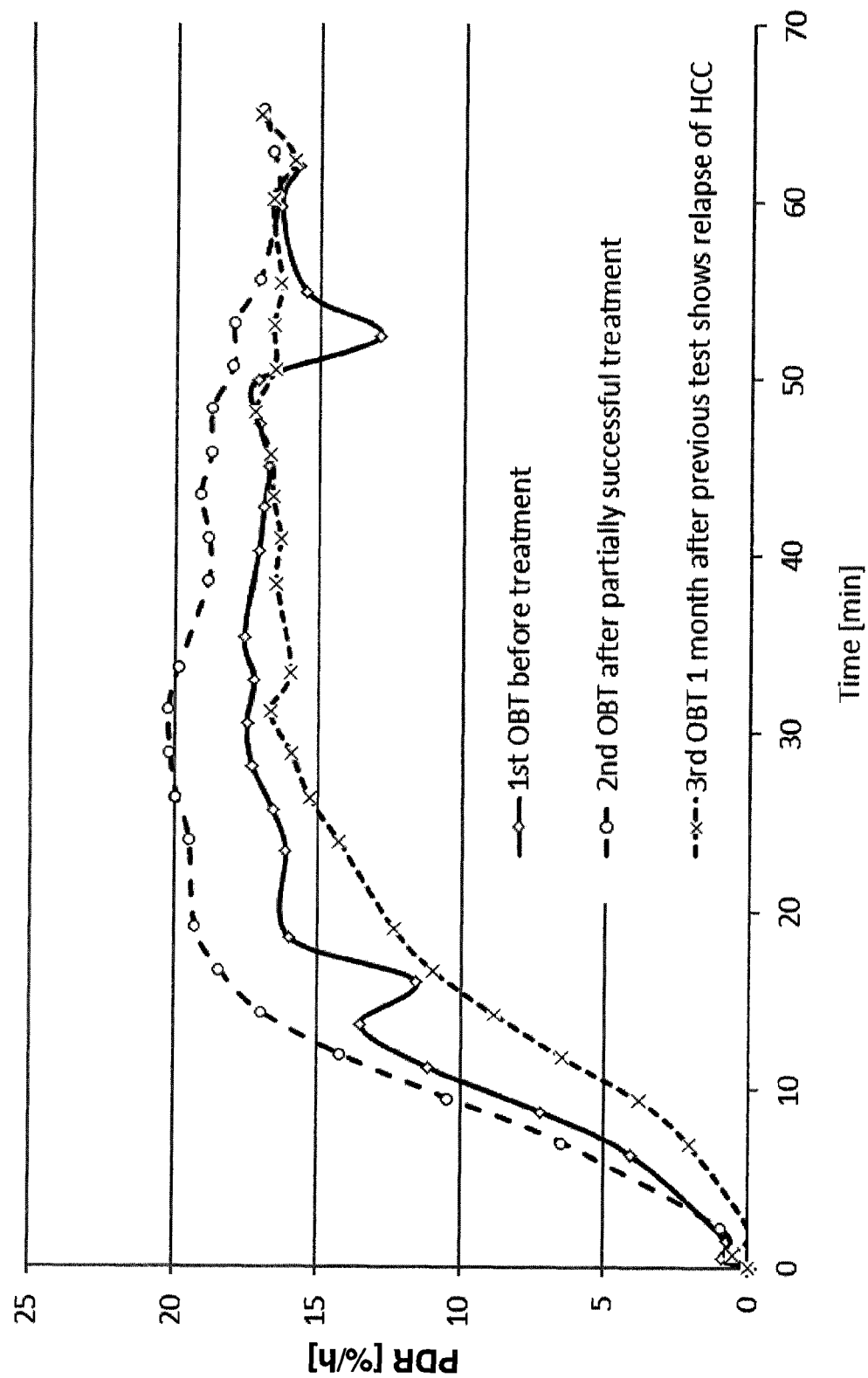
FIG. 7. PDR curves of three consecutive $^{13}$C-octanoate breath tests of a 69 year old female NASH patient with HCC, before and after treatment with relapse of HCC.

FIG. 7 shows PDR curves of three consecutive OBTs of a typical cirrhotic patient with liver cancer. All curves are low. Although TACE treatment showed some improvement in curve no. 2 ("$2^{nd}$ OBT treatment after partially successful treatment") the relapse of HCC can be clearly seen on the $3^{rd}$ curve ("$3^{rd}$ OBT 1 month after previous test shows relapse of HCC").

Figure 8:
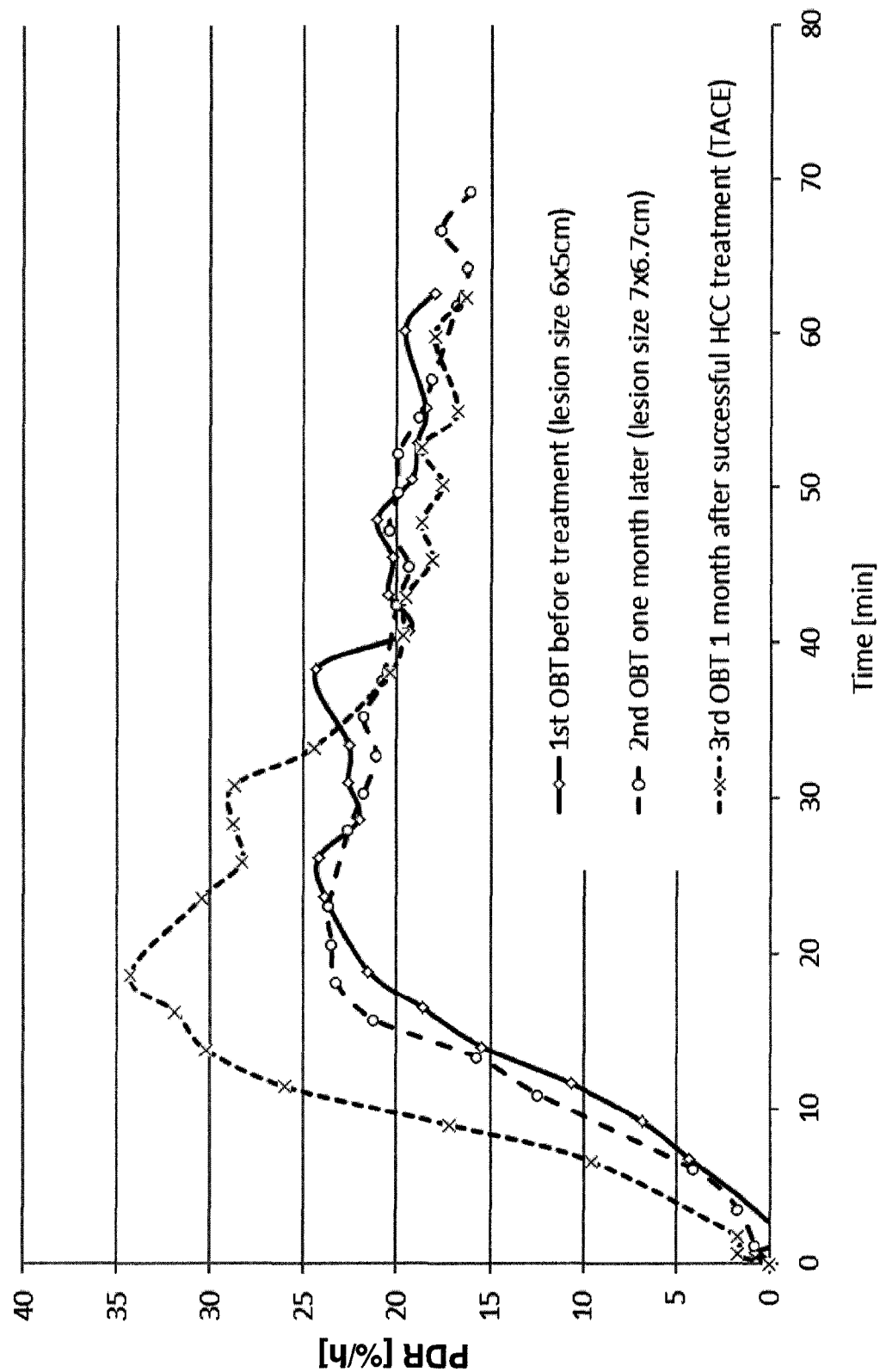
FIG. 8. PDR curves of three consecutive $^{13}$C-octanoate breath tests of a 61 year old male with cryptogenic cirrhosis, before and after successful HCC treatment.

FIG. 8 shows PDR curves of three consecutive OBTs of a typical cirrhotic patient with liver cancer who had a successful TACE treatment. Two curves before treatment are low. The third curve shows characteristics of a non-HCC case (high PDR Peak) and therefore points to the fact that the HCC treatment was successful. The lesion remained at 7 cm without growth and was in-active.

Figure 9:
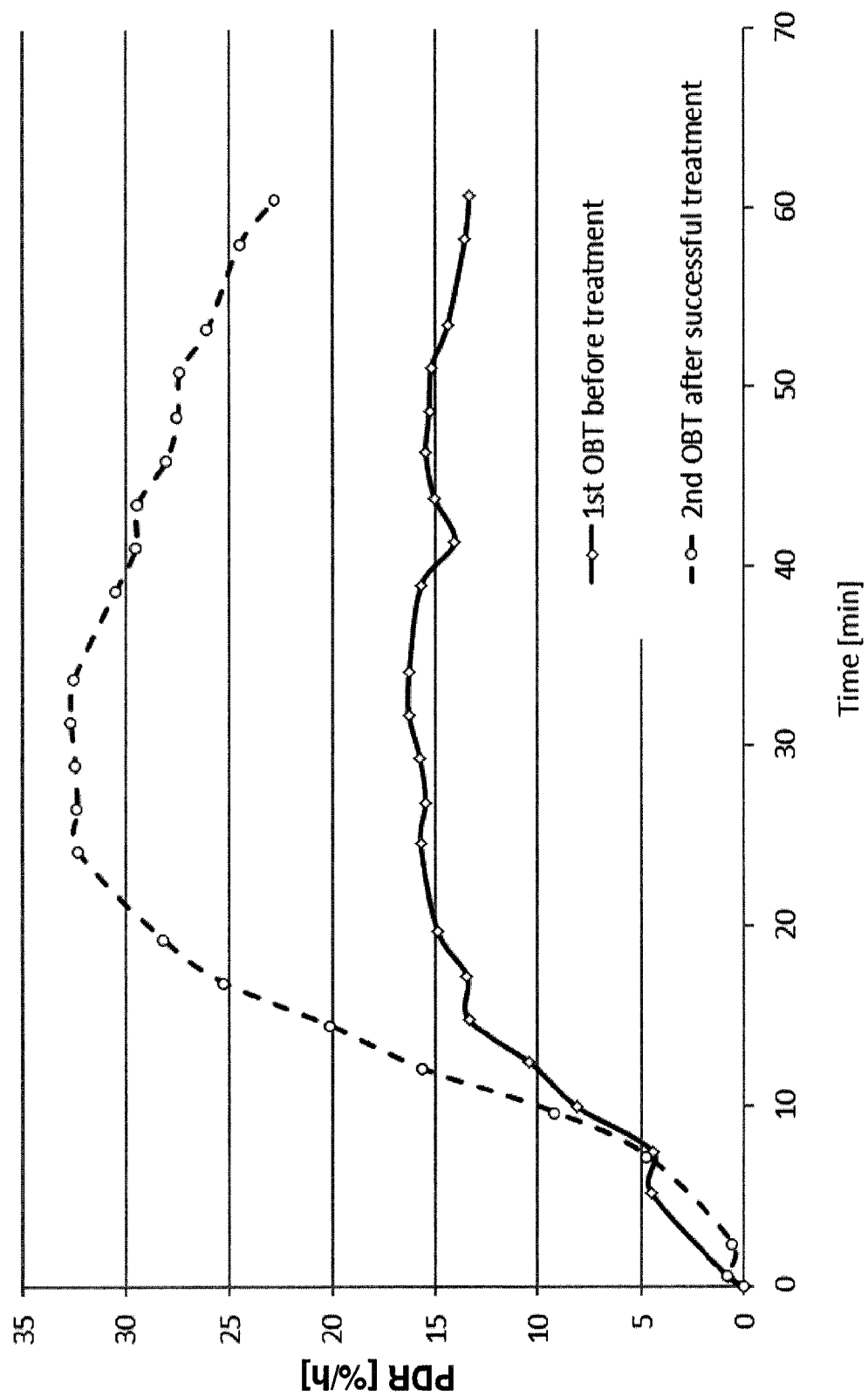
FIG. 9. PDR curves of two consecutive $^{13}$C-octanoate breath tests of a 58 year old male with HCV cirrhosis before and after successful HCC treatment.

FIG. 9 shows PDR curves of two consecutive OBTs of a typical cirrhotic patient with liver cancer who had a successful TACE treatment. The curve before treatment is low. The second curve shows characteristics of a non-HCC case (high PDR Peak) and therefore points to the fact that the HCC treatment was successful.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. A method for detection of hepatocellular carcinoma (HCC) in a subject, the method comprising the steps of:
   (i) administering an isotope-labeled octanoate to the subject;
   (ii) measuring a level of an isotope-labeled metabolic product of octanoate in exhaled breath of the subject following administration of the isotope-labeled octanoate;
   (iii) comparing the measured level of isotope-labeled metabolic product of octanoate in the subject to a reference level; and
   (iv) detecting hepatocellular carcinoma based on the measured level of isotope-labeled metabolic product of octanoate; wherein a significantly decreased level of isotope-labeled metabolic product of octanoate is indicative of active hepatocellular carcinoma; and wherein detecting hepatocellular carcinoma comprises distinguishing between impaired liver function caused by fibrosis or cirrhosis and hepatocellular carcinoma.

2. The method of claim 1, wherein said reference octanoate metabolism is a control octanoate metabolism determined in subjects not afflicted with HCC.

3. The method of claim 1, further comprising distinguishing between active and inactive hepatocellular carcinoma based on said comparing of the measured level of isotope-labeled metabolic product of octanoate to the reference level.

4. The method of claim 1, wherein the step of measuring is performed by continuous measurement over a predetermined period of time following a single administration of a labeled octanoate.

5. The method of claim 1, wherein a plurality of breath samples is collected from the subject at periodic intervals over a predetermined period of time following a single administration of a labeled octanoate.

6. The method of claim 1, wherein the isotope-labeled metabolic product is $CO_2$.

7. The method of claim 1, wherein the isotope-labeled octanoate is selected from the group consisting of carbon-13, carbon-14 and oxygen-18.

8. The method of claim 1, wherein the step of comparing octanoate metabolism in the subject to a reference octanoate metabolism comprises generating at least one of a delta over baseline (DOB) curve, a percentage dose recovery (PDR) curve and a cumulative PDR (CPDR) curve for the subject, and comparing at least one parameter of said DOB, PDR or CPDR to at least one parameter of reference DOB, PDR, CPDR curves and a combination thereof.

9. The method of claim 8, wherein the step of comparing octanoate metabolism in the subject to a reference octanoate metabolism comprises generating a PDR curve and comparing at least one parameter of said PDR curve to at least one parameter of a reference PDR, wherein the at least one parameter is selected from the group consisting of peak height, time of appearance of the peak and the slope of rate of metabolism.

10. The method of claim 9, wherein the parameter is selected from peak height and time to peak, and wherein a decreased peak height is indicative of HCC and a longer time to peak is indicative of HCC.

11. The method of claim 8, wherein the at least one parameter is selected from one or more PDR (% dose/hr) values at selected time points, one or more CPDR values at selected time points and one or more DOB values at selected time points, and wherein decreased PDR, CPDR and/or DOB values at the selected time points are indicative of HCC.

12. The method of claim 1, comprising performing a first evaluation of the liver function by monitoring an isotope-labeled metabolic product of octanoate in exhaled breath of the subject following a first administration of an isotope-labeled octanoate, and performing a second evaluation of liver function after a predetermined period of time by monitoring an isotope-labeled metabolic product of octanoate in exhaled breath of the subject following a second administration of an isotope-labeled octanoate.

13. The method of claim 12, wherein the step of performing a second evaluation after a predetermined period of time is repeated a multiplicity of times.

14. The method of claim 1, further comprising normalization of the values obtained in step (ii) according to disease etiology.

15. The method of claim 14, wherein the disease etiology is selected from the group consisting of NASH and NAFLD.

16. The method of claim 1, further comprising normalization of the values obtained in step (ii) according to one or more blood test results.

17. The method of claim 16, wherein the one or more blood tests are selected from the group consisting of fasting glucose levels, insulin levels, ALT levels, AST levels, ALP levels, GGTP levels, bilirubin levels, albumin levels and sodium levels.

18. The method of claim 1, further comprising normalizing measured levels of the isotope-labeled metabolic product based on a treatment that the subject is receiving or has received.

19. The method of claim 18, wherein the treatment is sorafenib administration.

20. The method of claim 1, wherein the subject is selected from the group consisting of a subject who is at risk of developing hepatocellular carcinoma, a subject who is suspected of having hepatocellular carcinoma, a subject who is afflicted with hepatocellular carcinoma that has not undergone treatment, and a subject who is afflicted with hepatocellular carcinoma that has undergone or is undergoing treatment.

21. The method of claim 20, wherein the treatment of the subject that has undergone or is undergoing treatment is other than surafenib administration.

22. The method of claim 1, wherein the subject has at least one chronic liver disease.

23. The method of claim 22, wherein the chronic liver disease is selected from the group consisting of NASH, NAFLD, hepatitis B, hepatitis C and cirrhosis due to any etiology.

24. The method of claim 22, wherein the chronic liver disease is other than NASH or NAFLD.

25. The method of claim 1, further comprising the step of monitoring total $CO_2$ in exhaled breath of the subject.

26. The method of claim 1, wherein said isotope-labeled octanoate is administered orally, intravenously or intra nasally.

* * * * *